US012706187B2

(12) United States Patent
Keller et al.

(10) Patent No.: US 12,706,187 B2
(45) Date of Patent: Aug. 11, 2026

(54) COMPUTER SYSTEM AND METHOD FOR EFFICIENT INDEX CREATION FOR A STREAMING DATABASE

(71) Applicant: Universität Zürich, Zürich (CH)

(72) Inventors: Emanuela Elisabeth Sophia Keller, Kilchberg (CH); Jens Michael Boss, Zürich (CH); Gagan Narula, Zürich (CH); Christian Strässle, Neuenhof (CH); Jan Folkard Wilms, Zürich (CH)

(73) Assignee: UNIVERSITÄT ZÜRICH, Zürich (CH)

( * ) Notice: Subject to any disclaimer, the term of this patent is extended or adjusted under 35 U.S.C. 154(b) by 10 days.

(21) Appl. No.: 18/735,772

(22) Filed: Jun. 6, 2024

(65) Prior Publication Data

US 2024/0321417 A1 Sep. 26, 2024

Related U.S. Application Data

(63) Continuation of application No. PCT/EP2022/071678, filed on Aug. 2, 2022.

(30) Foreign Application Priority Data

Dec. 9, 2021 (EP) .................................... 21213561

(51) Int. Cl.
*G16H 10/60* (2018.01)
*G06F 16/22* (2019.01)

(52) U.S. Cl.
CPC ......... *G16H 10/60* (2018.01); *G06F 16/2228* (2019.01)

(58) Field of Classification Search
None
See application file for complete search history.

(56) References Cited

U.S. PATENT DOCUMENTS 10,762,094 B1 * 9/2020 Kim ....................... G16H 15/00
11,120,908 B2 * 9/2021 Agnello ................. H04L 67/06
(Continued)

FOREIGN PATENT DOCUMENTS

JP 2006040128 A * 2/2006

OTHER PUBLICATIONS

JP2006040128 machine translation (Year: 2006).*
(Continued)

*Primary Examiner* — Jason S Tiedeman
(74) *Attorney, Agent, or Firm* — Brake Hughes Bellermann LLP

(57) ABSTRACT

Index creation in a streaming database with medical state parameters allows near-real-time access to medical state parameters reflecting medical states of patients. A message broker receives messages that include records with current measured medical state parameter values of patients. A stream processor processes messages with a plurality of parameter augmentation algorithms to derive additional computed medical state parameter values for a respective patient. Records with the computed values are inserted via generated messages into any incoming data stream. A data handler can create persisted patient-signal specific stream data tables for unknown combinations of patient identifier and signal identifier in the streaming database, and can create a block range index for the time information of the persisted stream data table. Records contained in the received and generated messages are written into respective persisted patient-signal specific stream data tables of the streaming database, and respective block range indexes are updated accordingly.

20 Claims, 8 Drawing Sheets

(56) References Cited

U.S. PATENT DOCUMENTS

| | | | | |
|---|---|---|---|---|
| 2003/0069758 | A1* | 4/2003 | Anderson | G16H 40/20 707/999.102 |
| 2011/0169644 | A1* | 7/2011 | Muhsin | G08B 25/008 340/573.1 |
| 2011/0288379 | A1* | 11/2011 | Wu | G16H 40/67 600/301 |
| 2013/0162433 | A1* | 6/2013 | Muhsin | G08B 25/008 340/573.1 |
| 2016/0354039 | A1* | 12/2016 | Soto | A61B 5/74 |
| 2017/0071546 | A1* | 3/2017 | Jain | A61B 5/0533 |
| 2018/0082036 | A1* | 3/2018 | Hanrahan | G16H 40/63 |
| 2018/0116560 | A1* | 5/2018 | Quinn | A61B 5/02055 |
| 2018/0246950 | A1* | 8/2018 | Arye | G06F 16/2272 |
| 2019/0079943 | A1* | 3/2019 | Snavely | G06F 16/24568 |
| 2019/0206570 | A1* | 7/2019 | Colister | G16H 10/60 |
| 2020/0168330 | A1* | 5/2020 | Schulman | G16H 10/60 |
| 2020/0204631 | A1* | 6/2020 | Subramaniam | H04L 67/02 |
| 2021/0244339 | A1* | 8/2021 | Szabados | A61B 5/6833 |
| 2021/0375446 | A1* | 12/2021 | Page | G16H 40/40 |
| 2022/0000435 | A1* | 1/2022 | Babaeizadeh | A61B 5/7235 |
| 2022/0086278 | A1* | 3/2022 | Chiu | H04M 3/5116 |
| 2022/0353000 | A1* | 11/2022 | Dharwad | A61B 5/0205 |

OTHER PUBLICATIONS

Cardenas, A. et al.: "Management of Streaming Body Sensor Data for Medical Information Systems," Jan. 1, 2003, retrieved from the internet on May 20, 2022, <http://citeseerx.ist.psu.edu/viewdoc/download?doi=10.1.1.93.8687&rep=rep1&type=pdf>, 6 pages.

Gorantla E.: "Postgres BRIN Index—Large Data Performance With Minimal Storage," retrieved from the internet <https://medium.com/geekculture/postgres-brin-index-large-data-performance-with-minimal-storage-4db6b9f64ca4>, Apr. 25, 2021, 19 pages.

Hamilton, P.: "Open source ECG analysis," Computers in Cardiology, 2002, 29, pp. 101-104.

International Search Report and Written Opinion from PCT/EP2022/071678 mailed Nov. 8, 2022, 12 pages.

Kucirka, L.M. et al.: "Variation in False-Negative Rate of Reverse Transcriptase Polymerase Chain Reaction-Based SARS-CoV-2 Tests by Time Since Exposure," Annals of Internal Medicine, 2020, 173(4): p. 262-267.

Mao, L. et al.: "Neurologic Manifestations of Hospitalized Patients With Coronavirus Disease 2019 in Wuhan, China," JAMA Neurolology, Apr. 10, 2020, 77(6), pp. 683-690.

Rogov, E.: "Indexes in PostgreSQL—9 (BRIN)," retrieved from the internet <https://habr.com/en/companies/postgrespro/articles/452900/>, Jun. 3, 2019, 24 pages.

* cited by examiner

| | {patient_id, | signal_id, | timestamp, | value} |
|---|---|---|---|---|
| M1: | | | | |
| [{ | P1, | Signal 1, | 2021-10-08T11:05:00.000, | 0.0383}, |
| { | P1, | Signal 1, | 2021-10-08T11:05:00.010, | 0.0483}, |
| { | P1, | Signal 1, | 2021-10-08T11:05:00.020, | 0.0323},...] |
| M2: | | | | |
| [{ | P1, | Signal 2, | 2021-10-08T11:05:00.000, | 1.0383}, |
| { | P1, | Signal 2, | 2021-10-08T11:05:00.010, | 8.0483}, |
| { | P1 | Signal 2, | 2021-10-08T11:05:00.020, | 3.0323},...] |

COMPUTER SYSTEM AND METHOD FOR EFFICIENT INDEX CREATION FOR A STREAMING DATABASE

CROSS-REFERENCE TO RELATED APPLICATION

This application claims priority to, and is a continuation of, PCT/EP2022/071678, filed on Aug. 2, 2022 and entitled "COMPUTER SYSTEM AND METHOD FOR EFFICIENT INDEX CREATION FOR A STREAMING DATABASE," which in turn claims priority to EP Application No. 21213561.0 filed on Dec. 9, 2021, both of which are hereby incorporated by reference in their entireties.

TECHNICAL FIELD

The present description generally relates to index creation for a streaming database, and in particular, relates to methods, computer program products and systems for partitioning a streaming database with medical state parameters of different types associated with a plurality of patients for efficient index creation to enable near-real time access to data sets of the streaming database.

BACKGROUND

Patients in intensive care units are typically monitored by using a plurality of medical devices for measuring all kinds of medical state parameters reflecting the medical state (or health status) of the respective patients. Different medical devices can provide raw measurement data at different sampling rates. Such measurement data associated with a plurality of patients in the intensive care unit are typically fed into one or more data streams. Often it is possible to derive additional medical state parameters of a patient from the received raw data. However, because of huge amounts of raw data and time delays caused by the enrichment of such raw data, the access to all relevant data in a streaming database reflecting the current medical state of a patient in near-real time is challenging. In critical care, high-resolution data such es electrocardiography (ECG), continuous blood pressure monitoring, data from artificial ventilation or long-term electroencephalography (EEG) signals are gathered in real time by multiple biosensors. The data streams, however, with a temporal resolution of milliseconds are complex and are conventionally visualized as curves on different monitoring devices. The signals, furthermore, are contaminated with different types of noise and artifacts. In order to describe the biological system and complex pathophysiology, they typically need to be pre-processed with advanced analytics, which is often time consuming.

It is thereby important to provide a comprehensive view on a patient's current medical state taking into account the measured medical state parameters and derived medical state parameters in near-real time. This is particularly important in an intensive care environment where a change of the patient's medical state may require immediate treatment by medically trained staff to save the patient's life.

SUMMARY

Hence, there is a need for a system and method to allow near-real time access to all medical state parameters of an intensive care patient reflecting the patient's current and past health status. When examining the health status of a patient, it is often necessary to retrieve data over longer periods of time in order to assess the development of certain medical state parameters. That is, near-real time data access is a requirement not only for medical state parameter values of the respective patient covering the last few minutes but rather covering longer periods such as hours or even days. Further, often results from data pre-processing are to be merged with information such as clinical characteristics and biomarkers. As an example, Heart Rate Variability (HRV) is such a specific feature, which can be extracted only from high frequency bio-signals. HRV describes changes in the time interval between two subsequent R-peaks in the ECG. Once time intervals are measured, they can be used to calculate various time-domain and frequency-domain metrics that characterize the HRV. For example, the herein disclosed method and system allow for the combination of the feature HRV with other multidimensional data as biomarkers to provide more accurate predictive algorithms for a medical (treatment) decision support system.

There can be situations where a deterioration of the medical state requires an immediate action by medically trained staff (e.g., within seconds rather than minutes) to save a patient's life. Near-real time as used herein, describes a near-real time system response in that a computation in response to a received input is only delayed by the time delay introduced, by automated data processing or network transmission, between the occurrence of an event and the use of the processed data, such as for display or feedback and control purposes. For example, a near-real-time display depicts an event or situation as it existed at the current time minus the processing time, as nearly the time of the live event (e.g., the measurement of a measured medical parameter value—i.e., the raw data—by the medical device). The above technical problem is solved by a computer system, a computer-implemented method and a computer as claimed in the independent claims.

In one embodiment, a computer-implemented method is provided for efficient index creation in a streaming database with medical state parameters of different types associated with a plurality of patients. The created index allows near-real-time access to medical state parameters reflecting the medical states of patients. The method is particularly advantageous in intensive care environments where time critical medical treatment decisions need to be taken in real-time for a plurality of patients. The computer-implemented method can be executed by a computer system which implements modules which are configured to perform functions for executing the steps described in the following.

Initially, a message broker of the computer system receives messages in one or more incoming data streams with each message comprising one or more records. Each record has at least: a current measured medical state parameter value of a particular patient being associated with time information reflecting the time of the respective measurement, a signal identifier indicative of the type of the current medical state parameter value, and a patient identifier associated with the particular patient. Typically, in an intensive care unit, many different medical devices produce a lot of raw measurement data for a plurality of intensive care patients. Such raw data can include, for example, electrocardiography (ECG) signals for monitoring the patient's heart activity, signals from photoplethysmography to measure pulse rate and blood oxygen saturation, arterial lines with pressure transducers to measure the arterial blood pressure and the heart's pump activity, signals from central venous catheters to estimate central venous pressure, thermistors to measure the body temperature, electroencephalography to measure brain activity and further signals of other signal types indicative of the patient's health status.

Typically, the different sensors provide the measured raw data at different sampling rates. Therefore, the size of messages may vary dependent on the sampling rates of the respective medical devices which deliver the records included in a current message. In the following, raw data sampled at high sampling rates are also referred to as high resolution raw data, and raw data sampled at low sampling rates are also referred to as low resolution raw data. Each message has a timestamp which represents the exact time when the message is created. Some medical devices also provide timestamps for each measurement value. In such case, the respective records in a message have timestamps which represent the exact point in time when the respective raw data measurement was performed. Some medical devices do not directly provide such time information about the exact measurement time. However, such devices provide metadata with regard to the respective sampling rate which is added to the message including the respective records. It is therefore possible to derive for each record the respective time of measurement based on the timestamp of the message and the sampling rate which is associated with the sensor providing said raw data with a respective signal type.

While the message broker is receiving the one or more data streams, a stream processor of the system performs processing steps on the incoming messages and generates new messages which are then inserted into the incoming data stream(s). Thereby, generated messages may even be inserted into a new additional data stream which is received by the message broker as an incoming data stream.

The stream processor first processes incoming messages with a plurality of parameter augmentation algorithms. Thereby, each parameter augmentation algorithm is adapted to process medical state parameter values of one or more particular types included in one or more incoming messages associated with a respective patient to derive additional computed medical state parameter values with respective signal identifiers for the respective patient. A parameter augmentation algorithm can implement a certain computation formula applied to parameter values of incoming records but it may also be implemented by a machine learning model which has been trained accordingly to make respective predictions with regard to further (computed) medical state parameter values of a patient indicative of the patient's overall health status including the risk of medical complications. Advantageously, the data stream of incoming messages is organized such that the data for each patient is provided in a separate sub-stream. For example, a particular parameter augmentation algorithm can be configured to detect R-peaks in the raw data reflecting the ECG signal of a particular patient and compute corresponding inter-beat intervals. A further parameter augmentation algorithm can be configured to compute various HRV features on the basis of computed inter-beat intervals. Multiple parameter augmentation algorithms can operate on the incoming messages in parallel. It is also possible, that two or more parameter augmentation algorithms are sequentially lined up so that only the first algorithm directly processes incoming messages and a second algorithm processes the output of the first algorithm, a third algorithm processes the output of the second algorithm, and so on. The output of a parameter augmentation algorithm is a computed medical state parameter value of said patient which is based on values (measured medical parameters (raw data) and/or computed medical parameters) of records in incoming messages.

The stream processor then inserts generated messages into any incoming data stream. Each generated message includes one or more records, with each record having a respective computed medical state parameter value with respective signal identifier, the patient identifier indicative of the respective patient, and time information based upon the one or more incoming messages associated with the respective patient. Inserting a generated message into an incoming data stream results in an additional message received by the message broker. That is, this generated message becomes available to be further processed by the stream processor. This allows for an iterative enrichment of the medical parameters because the parameter augmentation algorithms can be adapted to compute further computed medical parameters on the basis of previously computed medical parameters which are all based on originally measured raw data received from respective sensors.

As the originally measured raw data with the respective time information reflecting the time of the measurement is not available anymore when a corresponding generated message with computed medical state parameters comes in, the stream processor computes the time information in the generated message based upon the one or more incoming messages associated with the respective patient. In other words, the original time information associated with the underlying raw data records is propagated into the corresponding records of the generated message. This is advantageous as, later on, all medical state parameters (original raw data and computed data) of a particular patient which relate to the same time of measurement can be reconciled in near-real time to provide an accurate medical state overview of said patient at a particular point in time.

For example, in one implementation, the time information associated with a particular record of a particular generated message can be computed from the time information associated with the respective records of the one or more incoming messages associated with the respective patient via interpolation of the time series associated with said respective records. In an alternative implementation, the time information of a record of the generated message may be set to the time associated with the latest record of the one or more incoming messages associated with the respective patient.

A data handler of the system ensures that all records of the received messages (the messages including medical state parameter values in the form of measured raw data) and generated messages (the messages including computed medical state parameter values) are written to respective persisted data tables of the stream database with an index that allows near-real time access to all (i.e., measured and computed) medical state parameter values of a patient reflecting the patient's past, current and future health status. To achieve this, the data handler performs a partitioning of the streaming database into persisted patient-signal specific stream data tables. A persisted stream data table, as used herein, is a database table in which the database engine of the streaming database physically stores records of the incoming messages. If a particular record contained in the received and generated messages refers to a yet unknown combination of patient identifier and signal identifier, a respective persisted patient-signal specific stream data table is created in the streaming database. A yet unknown combination of patient identifier and signal identifier (i.e., the combination not yet known by the streaming database) may be received by the data handler when a new patient has arrived in the intensive care unit and the first raw data have been measured for that patient, or a new signal type is provided for an already known patient. The data handler also creates a block range index for the time information of said persisted patient-signal specific stream data table.

The records contained in the received and generated messages are then written into respective persisted patient-signal specific stream data tables of the streaming database. Finally, the streaming database updates the block range index of a respective persisted patient-signal specific stream data table each time a record has been inserted in said persisted data table. The described partitioning of the streaming database into patient-signal specific stream data tables is not only advantageous in that it allows near-real time access to the records related to a particular medical state parameter for a particular patient in a particular time interval. It also provides the further advantage that, because of the high granularity of the target stream data tables all records in the incoming messages which relate to different combinations of patient identifier and signal identifier can be written to the respective persisted target stream data tables in parallel because a write operation on a particular patient-specific data stream table does not cause a lock to any other patient-specific data stream table. This allows extremely fast writing of the huge number of records into the streaming database. In combination with a block range index-based (BRIN) access to the records, near-real time monitoring of each patient in the intensive care unit is achieved. For example, the medical parameters and their development over time can be visualized via corresponding graphical representations on an appropriate display. Typically, such monitoring display shows a dense representation of all relevant vital parameters of a patient and has integrated with alarm functions which immediately raise an alarm if one or more medical state parameter values exceed predefined thresholds indicating the normal range of such parameters.

In one embodiment, a virtual stream data table of the streaming database is used as a common interface to the persisted patient-signal specific stream data tables. Such a virtual data table of the streaming database does not physically store data like a persisted data table but rather defines the structure of the data and provides the information about how the data is distributed between the various persisted data tables. A virtual data table has a data access method which defines how to retrieve data. When writing to the virtual stream data table, the streaming database automatically writes such data into the appropriate corresponding persisted data tables and also reads the data from such persisted tables.

In one embodiment, the data handler partitions the virtual stream data table by patient identifier into a plurality of (virtual) patient specific stream data tables. Further, the data handler partitions each patient specific stream data table by signal identifier into a plurality of (persisted) patient-signal specific stream data tables for which the BRIN indexes are created.

In real-world intensive care environments, it can happen that the same patient is registered with two different data collectors (e.g., each data collector can read the data of an associated CNS-Monitor of a Component Neuromonitoring Systems which is able to record data of modalities of different manufacturers). For example, a patient may be registered at a first data collector. When the patient is moved to another bed site, the patient should be unregistered in the first data collector and registered at a second data collector associated with the new bed site. However, sometimes unregistering is forgotten and two data collectors provide data for (at the first glance) the same patient simultaneously where in the given example the first data collector would actually provide data associated with another patient. In such case it is advantageous, when each record further comprises a bed identifier indicative for a patient bed site associated with the current measured medical state parameter value of said record. This allows to still separate the data for different patients. Some examples of commercially available data collectors are: eICU program by Philips, Böblingen, Germany; CNS Monitor by Moberg ICU solutions, Ambler, PA 19002 USA. Some data collectors have been developed in research projects: ICM+ by the University of Cambridge, UK; PhysioBank by MIT Laboratory for Computational Physiology, Boston, USA; PONI-Web infrastructure by Carleton University, Ottawa, Canada.

In one embodiment, the data handler is configured to create a monitoring session for a particular bed site over a time interval during which data is collected from the particular bed site without intermittency and or interruption.

Further aspects of the description will be realized and attained by means of the elements and combinations particularly depicted in the appended claims. It is to be understood that both, the foregoing general description and the following detailed description are exemplary and explanatory only and are not restrictive of the description as described.

DETAILED DESCRIPTION

Figure 1:
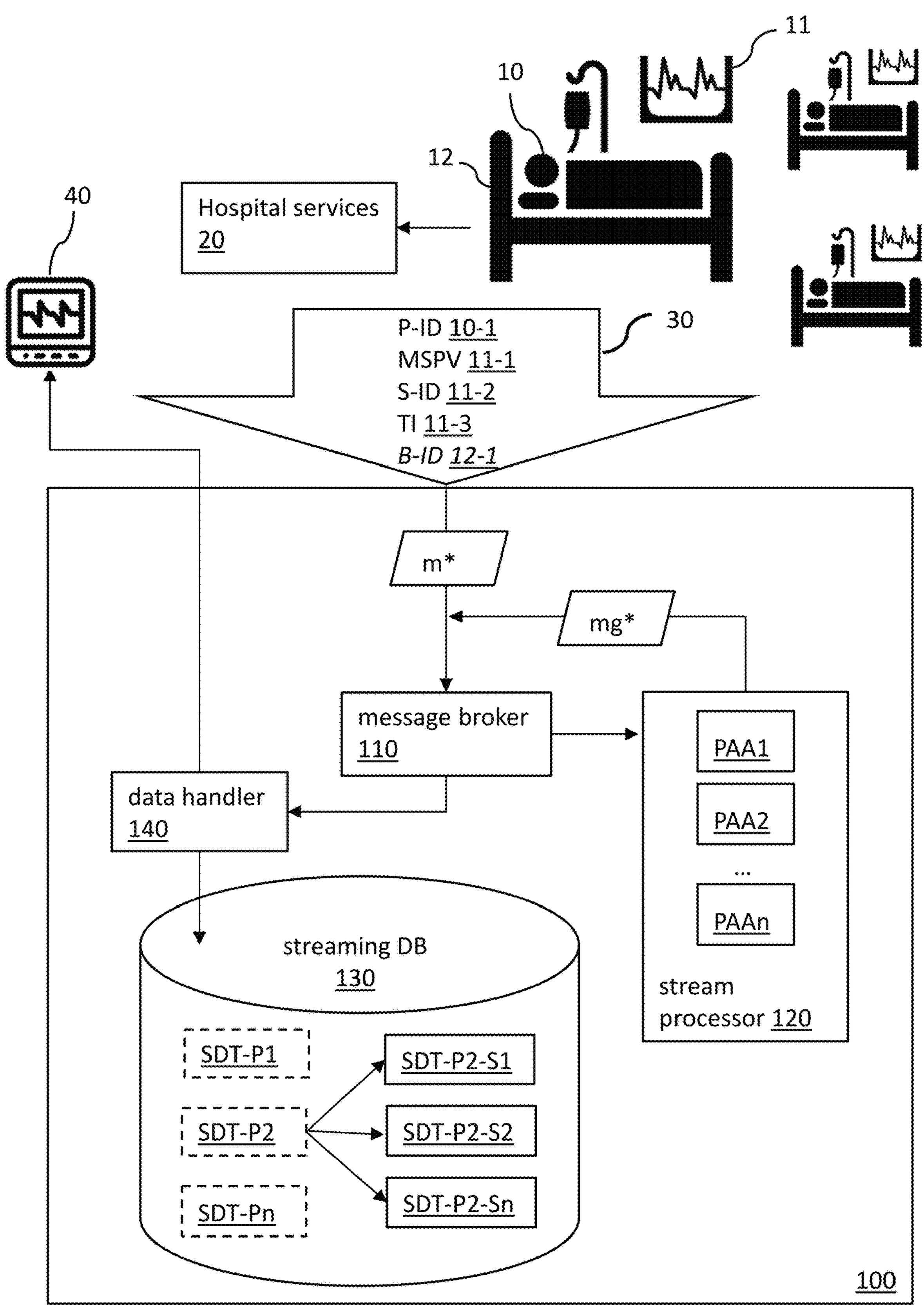
FIG. 1 shows a simplified diagram of a computer system for efficient index creation in a streaming database with medical state parameters of different types associated with a plurality of patients according to an embodiment.
Figure 2:
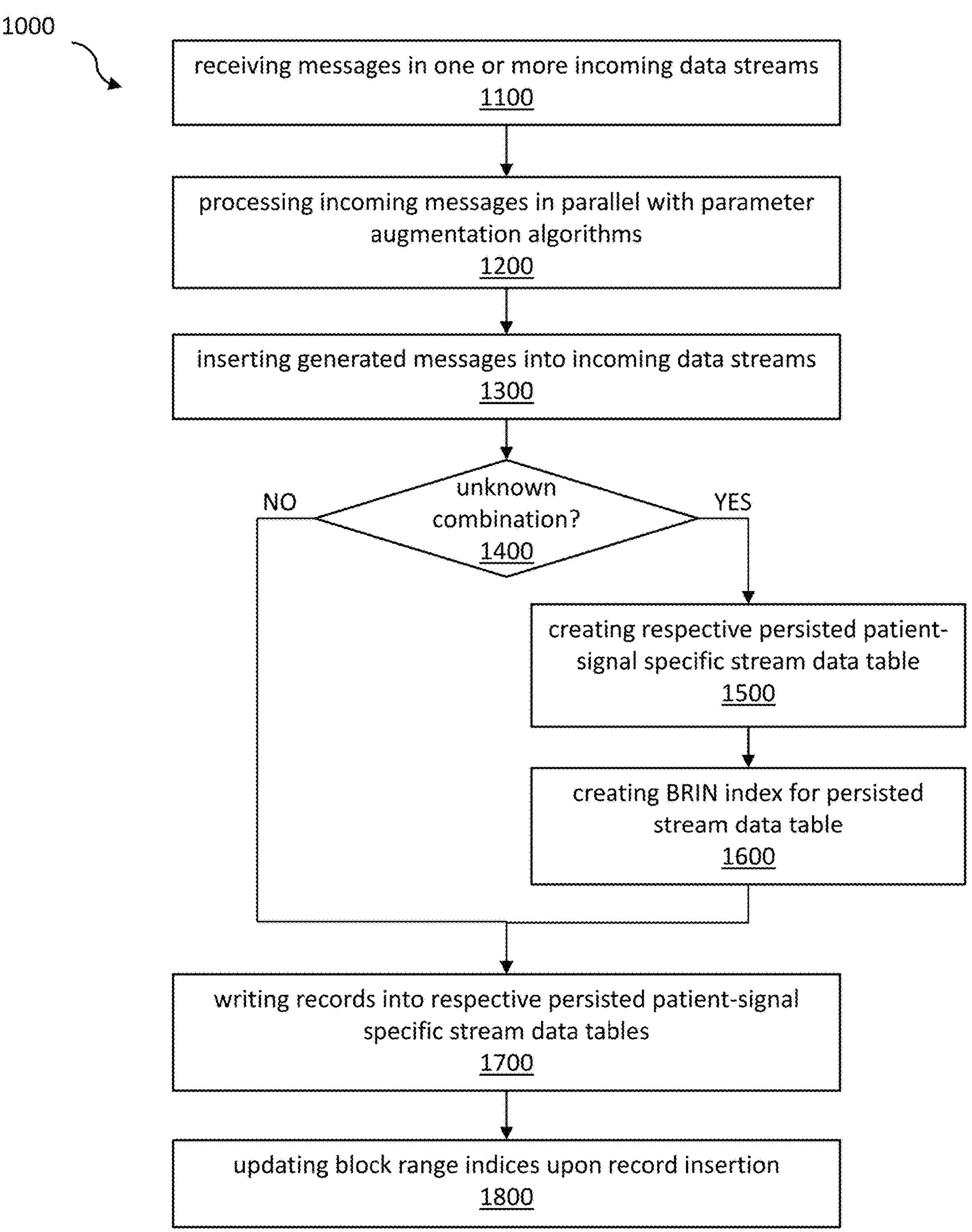
FIG. 2 is a simplified flowchart of a computer-implemented method for efficient index creation in a streaming database with medical state parameters of different types associated with a plurality of patients according to an embodiment.

FIG. 1 shows a simplified diagram of an embodiment of a computer system 100 for efficient index creation in a streaming database 130 with medical state parameters of different types associated with a plurality of patients 10. The stream data to be stored in the steaming database 130 typically reach a size in the order of Terabytes. Using classic indexing methods (e.g., B-trees) quickly leads to memoryinefficient indexes whose size exceeds the size of the stream data table(s). A memory-efficient near-real time access is not possible with such classic indexing. The herein disclosed system 100 allows near-real-time access to the medical state parameter values reflecting the medical states of said patients. FIG. 2 is a simplified flowchart of a computer-implemented method 1000 for efficient index creation in the streaming database 130. The method 1000 can be performed by system 100. The following description describes the system 100 in the context of method 1000 and, therefore, refers to reference numbers of FIG. 1 and FIG. 2.

The system 100 is communicatively coupled with medical devices 11 which provide medical state parameter values as part of one or more data streams 30 to the system 100. The medical devices 11 are operated in an intensive care environment around intensive care bed sites 12 with patients 10 receiving intensive care treatment. In FIG. 1, three beds with intensive care patients monitored by respective medical devices are illustrated. The reference numbers 10, 11, 12 are only shown for one bed site. In a real intensive care environment, each bed site 12 which is populated with a patient 10 who is associated with respective medical monitoring devices 11 providing medical state parameter values (raw data) measured for said patient 10. Further medical state parameter values (raw data) for a patient may be provided by hospital services 20, such as for example services provided by a laboratory (e.g., blood analysis, MRT data, etc.) based on patient specific measurements.

All such raw data measurement values are inserted as records into messages m* which are provided by the one or more data streams 30 to the system 100 via one or more appropriate interfaces known by a person skilled in the art. Each message may include a different number of records. The number of records in a message depends to some extent on the sampling rate used for the measurement of the respective medical state parameter values. Each record includes: a patient ID (P-ID) 10-1 identifying the patient for which the measurement was recorded, a current measured medical state parameter value (MSPV) 11-1 representing the value measured by a medical device 11 or derived via hospital services 20, a signal identifier (S-ID) 11-2 indicative of the type of the current medical state parameter value, and time information (TI) 11-3 reflecting the time when the respective measurement was made. In an optional embodiment, a record may further include a bed identifier indicative of the bed site which occupied by the patient with said P-ID.

Figures 3, 4:
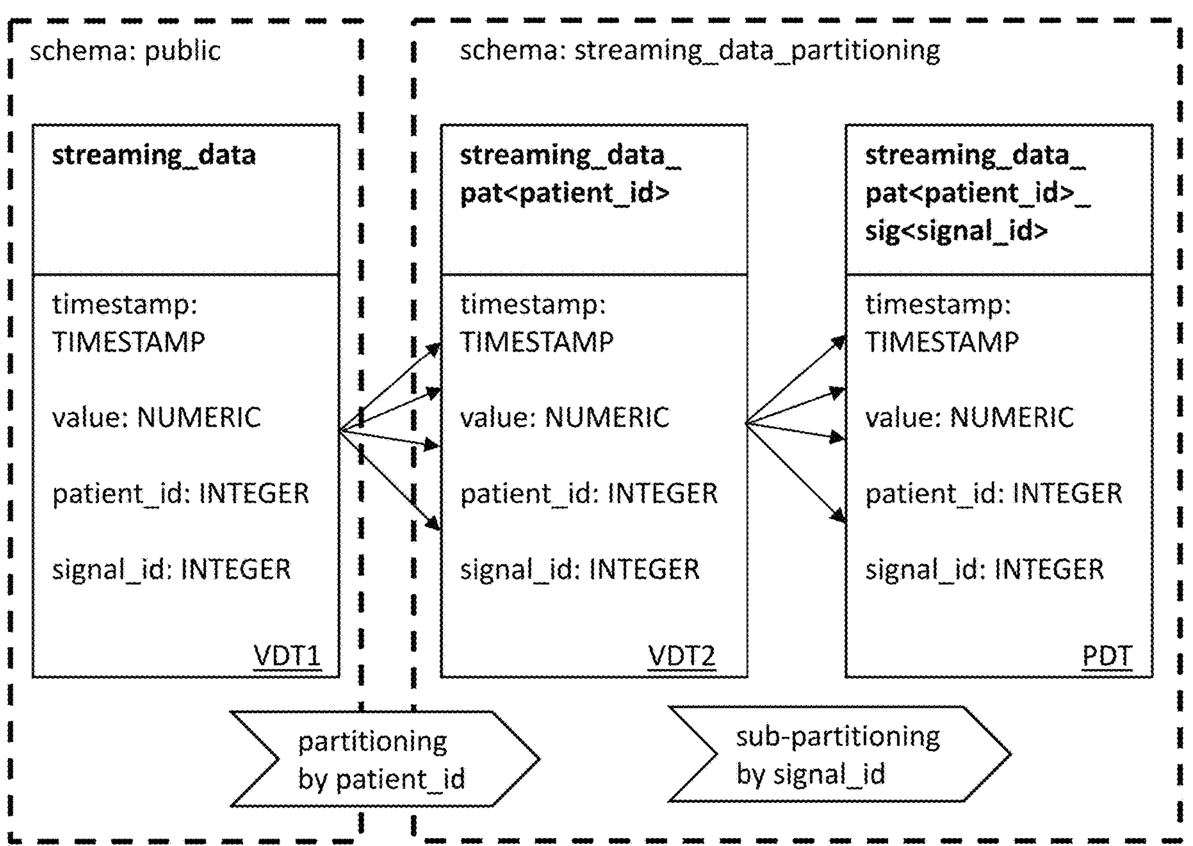
FIG. 3 illustrates an example partitioning schema with stream data tables according to an embodiment using virtual tables.
FIG. 4 illustrates example messages with simplified example records.

A message broker 110 of system 100 is adapted to receive 1100 messages in one or more incoming data streams 30. The message broker 110 may be implemented as an Apache Kafka message broker or by using Event Hubs provided by the Microsoft Cloud. A skilled person may also use other appropriate implementations. As mentioned above, each incoming message includes one or more records and each record includes the information about a particular medical state parameter measurement for a particular patient. Turning briefly to FIG. 4, two abstracted example messages M1, M2 are shown. In message M1, the three illustrated records relate to patient "P1" and signal type "Signal 1". The time information "2021-10-08T11:05:00.000" associated with the first record of M1 indicates that the measurement value MSPV: 0.0383 was taken on Oct. 8, 2021 at 11:05:00.000 am. In this example, each record has an absolute timestamp as time information. "Signal 1" is thereby sampled every hundredth of a second. Message M2 includes for the same patient "P1" measurements of another medical state parameter (of signal type "Signal 2"). In the example, the measurements of "Signal 2" occur simultaneously with the measurements of "Signal 1" at the same sampling rate. However, the respective records ended up in two different messages. Often a message includes only records of a particular signal type for a particular patient. This depends to some extent on how the medical devices performing the measurements are providing their data to the message broker. However, for the proposed approach it is irrelevant which data records are included in a particular message. The herein disclosed indexing approach also works for messages including records of multiple patients and multiple signal types.

Figure 6A:
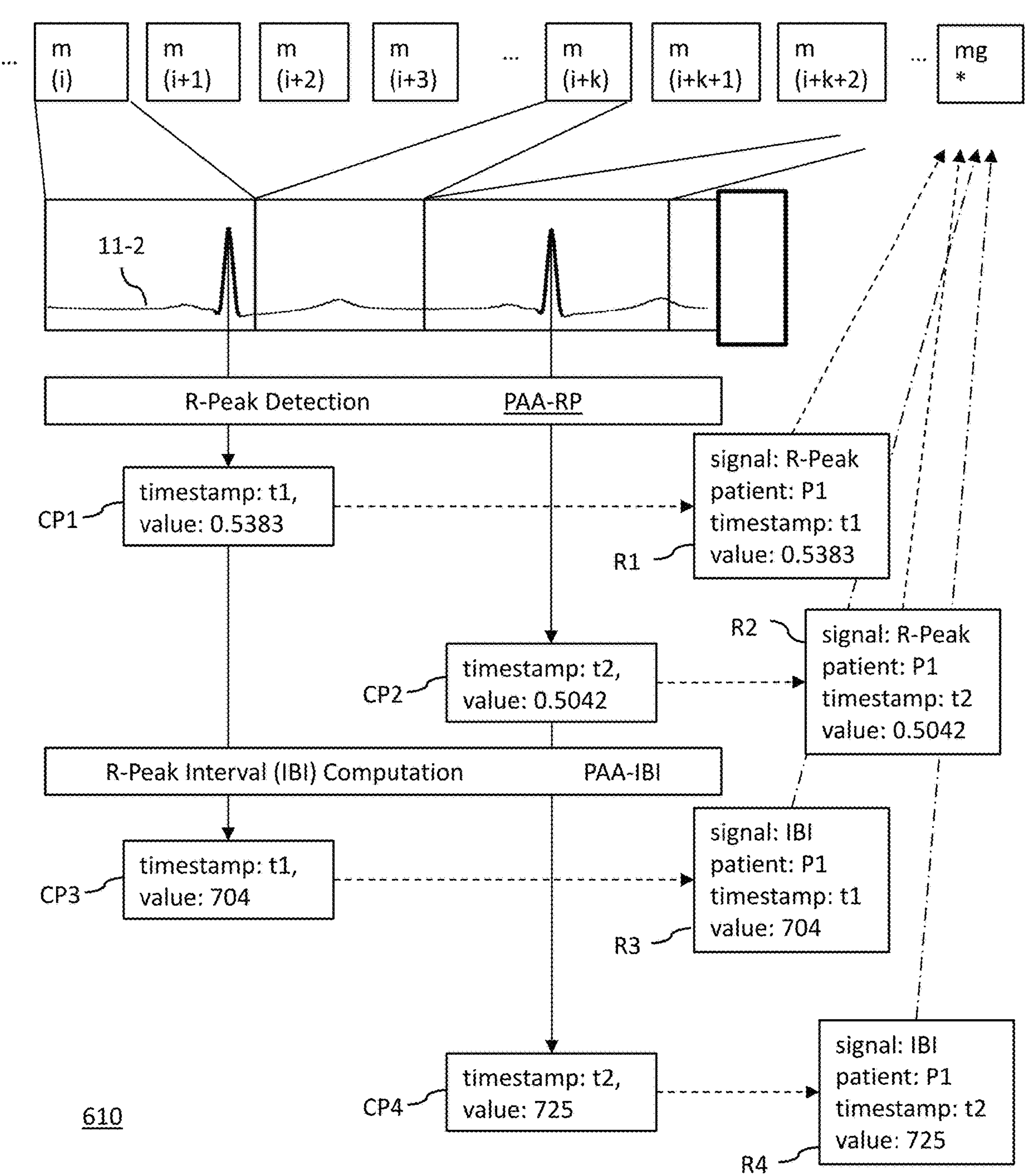
FIG. 6A illustrates a simplified example for parameter augmentation using a multi-stage parameter augmentation approach with setting time information to the time associated with the latest record of incoming messages.
Figure 6B:
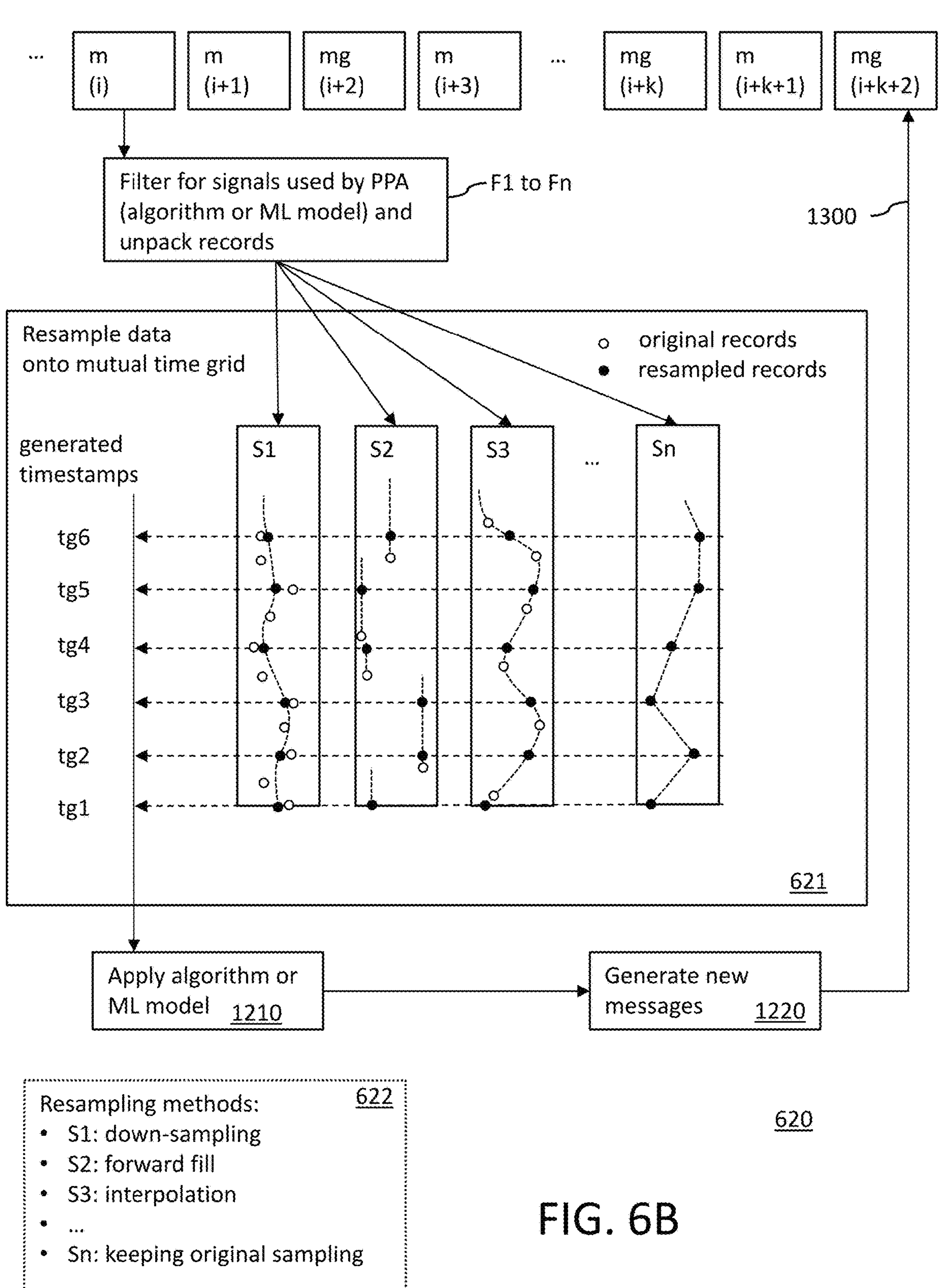
FIG. 6B illustrates the use of various resampling methods for setting the time information in records of generated messages.
Figure 6C:
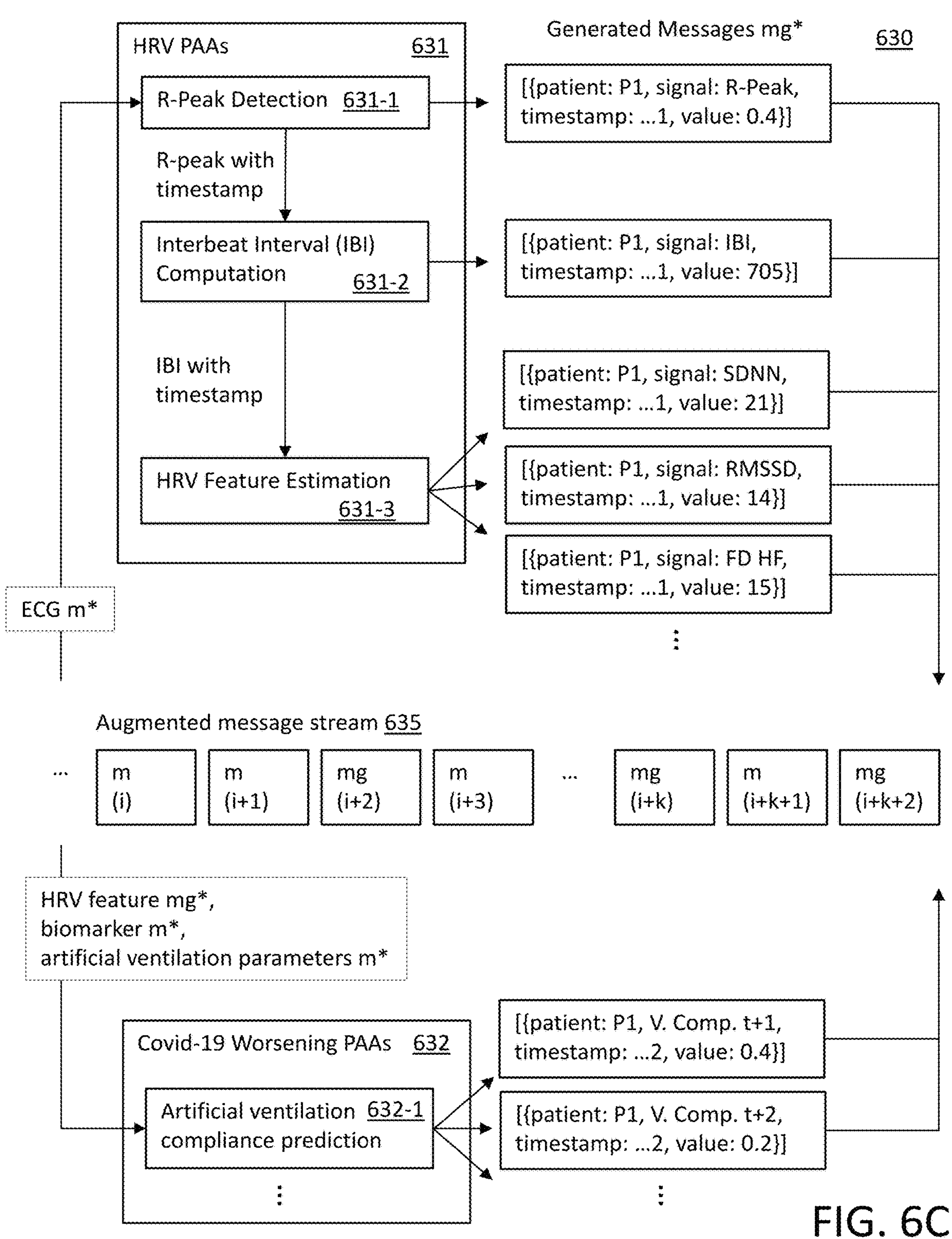
FIG. 6C illustrates an example using mix of multi-stage parameter augmentation based on raw data parameter values and single stage parameter augmentation based on raw data and computed parameter values.

Turning back to FIG. 1, a stream processor 120 of system 100 is adapted to access and further process the incoming messages received by the message broker 110. The stream processor 120 has a plurality of parameter augmentation algorithms PAA1 to PAAn which can process 1200 the incoming messages in parallel. Incoming messages which are received directly via the one or more data streams form the hospital services 20 or the medical devices 11 (i.e., messages which include records with values of measure raw data) are indicated in FIG. 1 with the reference sign m*. Each parameter augmentation algorithm is adapted to process medical state parameter values of one or more particular types 11-2 included in one or more incoming messages. As can be seen from the message example in FIG. 4, each MSPV 11-1 in a record of a message is associated with a respective patient. Based on such MSPVs, each parameter augmentation algorithm is adapted to derive additional computed medical state parameter values with respective signal identifiers for the respective patient. As a result, a new record with a computed medical state parameter (the output of the respective parameter augmentation algorithm) is generated. Such a new record includes the computed medical state parameter value with the respective signal identifier, the patient identifier indicative of the respective patient, and time information based upon the one or more incoming messages associated with the respective patient. FIGS. 6A to 6C illustrate alternative embodiments for deriving the time information of a record with a computed (derived) medical state parameter and are described in more detail further down below.

The computed medical state parameter values may again be useful as inputs for further processing by one or more of the parameter augmentation algorithms. Therefore, the stream processor 120 generates new messages mg* with each generated message including one or more records with computed medical state parameter values. The generated messages mg* are then inserted 1300 into any incoming data stream 30. After insertion, each generated message mg* is received by the message broker from where it can be accessed again by any parameter augmentation algorithm of the stream processor 120. In other words, the stream processor enriches the incoming data stream with additional medical state information of the intensive care patients 10 which was not yet available in the original raw data included in the received messages m*. That is, a parameter augmentation algorithm which requires as an input a mix of original raw data and computed medical health is now provided with that information by the message broker as both, the original raw data messages m* and the generated messages mg* with computed medical state parameters are included in the overall stream of incoming messages. This type of data enrichment can include multiple loops in that computed values serve as input for a PAA which delivers further computed values in records of a generated message being inserted into the incoming data stream(s). Then, this newly generated messages are again received by the message broker as incoming messages and may again serve as an input for PAA to derive further computed medical parameter values for a respective patient. There is no limit with regard to the number of loops for providing enriched medicals status data for such patient. The parallel processing of the incoming messages m* and mg* by the parameter augmentation algorithms PAA1 to PAAn allows for near-real time enrichment of the originally received raw data with additional derived medical status parameters providing an improved health monitoring of the intensive care patients. The stream processor provides a basic function which finally enables the system to provide medically trained staff can with relevant health information of each patient in near-real time so that immediate treatment actions can be started in case of an emergency with a patient transitioning into a critical health state. Such health information can be provided to the medically trained staff via an appropriate User Interface 40. The user interface 40 may support different modalities that allow to provide such information visually (e.g., graphics, text, etc.) or via audio (sound, speech, etc.).

However, there is still an issue to make all received raw data and corresponding derived medical status parameter accessible in near-real time so that all data of different signal types describing a patient's health condition at a given point in time can be visualized on a monitoring display in near-real time. This issue is solved by a data handler 140 of the system 100 which receives all original raw data messages m* and the generated messages mg* from the message broker 110. The data handler 140 for each message m*, mg*, the data handler 140 checks 1400 if the message includes a record related to a yet unknown combination of patient identifier and signal identifier. If "YES", that is, if for said combination no record has been stored so far in the streaming database 130, the data handler creates 1500 a respective persisted patient-signal specific stream data table (e.g., SDT-P2-S1 to SDT-P2-Sn) in the streaming database 130. From then on, the created persisted patient-signal specific stream data table is used to physically store all records in the messages which relate to said combination of patient identifier and signal identifier. Further, the data handler creates 1600 a block range index for the time information of the newly created persisted stream data table. A BRIN index is applicable to a data table storing a large number of records and where the index key value can easily be sorted and evaluated with a MinMax function. Moreover, a BRIN index is most useful when the index key values are already stored in an ordered manner. In the herein proposed approach, this is achieved by the partitioning of data by patient and signal type so that the data is already appropriately sorted when being stored in the persisted data stream tables. For example, the BRIN index for the time information of a particular persisted stream data table may use time windows adjusted to the sampling rate of the respective signal type. Thereby, for high resolution signal types the time windows are typically smaller than for low resolution signal types.

After the new persisted stream table has been created with the respective BRIN index, the record with the so far unknown combination is written 1700 into the new persisted stream data table. Any record contained in the messages m*, mg* which relates to an already known combination (i.e., check 1400 results in "NO" because at least one record with that combination has already been stored earlier in the streaming database and the respective patient-signal specific data table has already been created) is directly written 1700 by the data handler into the respective persisted patient-signal specific stream data table. Once record has been written (inserted) into a persisted patient-signal specific stream data table, the corresponding BRIN index is updated by the streaming database 130.

The proposed partitioning of the records into persisted patient-signal stream data tables is leading to highly granular relatively small data tables which in combination with the BRIN index for the time information, is advantageous when writing the records to the streaming database (less delays due to locked tables as described earlier) and when retrieving data for near-real time use (immediate access to all relevant data of a given signal type for a given patient during a given time interval).

In one embodiment, the data handler 140 performs data partitioning on the records in the incoming messages m*, mg* in two stages. In this embodiment, firstly, the data handler partitions a virtual stream data table by patient identifier 10-1 into a plurality of virtual patient specific stream data tables SDT-P1 to SDT-Pn. Further, the data handler partitions each virtual patient specific stream data table SDT-P2 by signal identifier 11-2 into a plurality of persisted patient-signal specific stream data tables SDT-P2-S1 to SDT-P2-Sn. All records of the incoming messages are then stored in the corresponding persisted stream data tables of the streaming database 130 in accordance with the corresponding block range index (BRIN).

FIG. 3 illustrates an example embodiment for data portioning in the streaming database with a virtual stream data table of the streaming database being used as a common interface to the persisted patient-signal specific stream data tables. The virtual stream data table "streaming_data" uses a schema "public" and defines the data structure VDT1 of "streaming_data". Each record of "streaming_data" has a timestamp (type TIMESTAMP), a value (type NUMERIC), a patient_id (type INTEGER) and a signal_id (type INTEGER). The virtual stream data table "streaming_data" is then partitioned into the persisted patient-signal specific stream data tables "streaming_data_pat<patient_id>_sig<signal_id>" which have data structures PDT that match the data structure VDT1 of the virtual stream data table. In the example of FIG. 3, the partitioning into the patient-signal specific stream data tables is governed by the schema "streaming_data_partitioning" which uses a further layer of virtual stream data tables. This further layer results from partitioning the original stream data table by patient_id into a plurality of virtual patient virtual patient specific stream data tables "streaming_data_pat<patient_id>" with data structures VDT2 also matching VDT1. Each virtual patient specific stream data table is then finally partitioned by signal_id into the plurality of persisted patient-signal specific stream data tables.

In this embodiment, the data handler initially checks if the patient_id of a record is already known in the streaming database. If not, a corresponding virtual patient specific stream data table is created before the respective persisted patient-signal specific stream data table is created. The record is written by the data handler to the original virtual stream data table VDT1. The streaming database then automatically stores the record in the respective persisted patient signal specific data stream table PDT (i.e., the one for the combination of patient_id and signal_id in said record).

Figure 5:
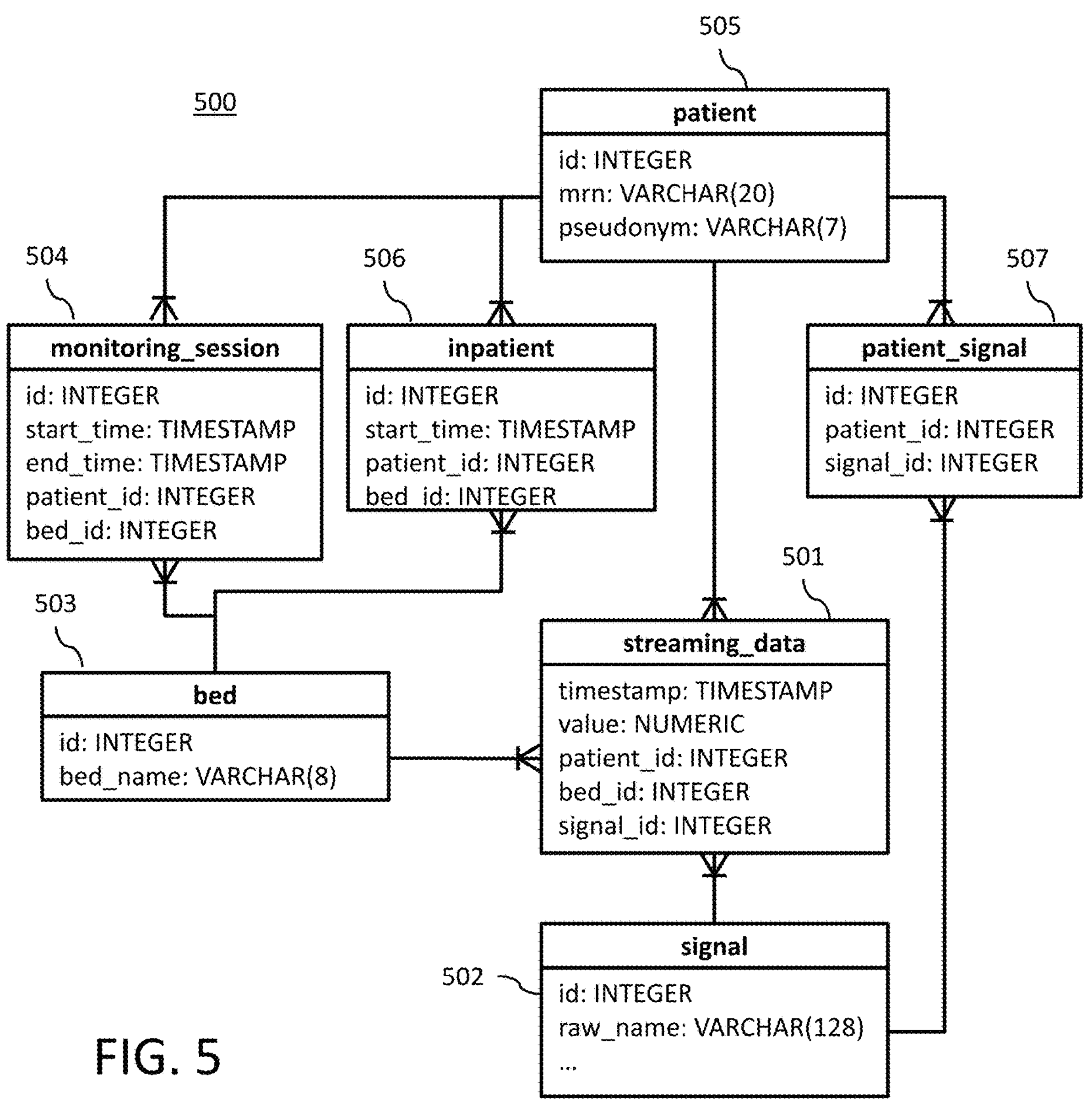
FIG. 5 is a simplified database schema of a streaming database according to an embodiment.

FIG. 5 illustrates a simplified database schema 500 for an optional embodiment of the streaming database. In this embodiment, the central streaming data table 501 also includes a bed identifier bed_id indicative for a patient bed site specified in table bed 503. That is, in this embodiment, the current measured medical state parameter value of a record is associated with the respective patient_id, bed_id, signal_id and the record's timestamp. The patients and signals are further specified in the respective tables 505, 502. The patient signal table 507 is used for storing patient-signal combinations which are known by the streaming database. The table monitoring session 504 is used to store the information about completed monitoring sessions for a particular patient_id and bed site over a time interval during which data is collected from the particular bed site without intermittency and or interruption. 504 records the start_time and end_time of such time intervals which qualify as monitoring sessions. The table inpatient 506 holds the information about currently monitored patients, thus reflecting ongoing monitoring sessions.

FIG. 6A illustrates an example 610, where two PAAs process ECG raw data records of a patient P1 in a message sub-stream ( . . . m(i) . . . m(i+k+2) . . . ) for a patient P1. Typically, the records associated with a particular patient are received such that the respective messages for this particular patient are provided in a separate sub-stream. The ECG raw data records reflect the measured ECG signal values 11-2 over time. The records are processed by a first parameter augmentation algorithm PAA-RP which is adapted to detect R-peaks in the original ECG signal. A first R-peak is detected at time t1 (the timestamp of the respective raw data record) with a peak value of "0.5383". The determined peak value at t1 corresponds to a computed medical state parameter CP1 of P1. A second R-peak is detected at time t2 with a peak value of "0.5042" which represents a second computed medical state parameter CP2 of P1. The data processor inserts the corresponding records R1, R2 with the computed R-peak values into one or more generated messages mg* (which are then inserted into the incoming data streams as illustrated by the dashed arrows). The first record R1 specifies the signal type "R-Peak" for the computed value "0.5383". The timestamp t1 which is assigned to the record R1 is derived from the original raw data record which represents the detected peak value. The same procedure is used for generating record R2. For example, for detection the R-Peaks, PAA-RP may be implemented by a custom version of the Hamilton algorithm. The ECG signal is first bandpass filtered. Subsequently, the derivative of the filtered signal is computed. Diverting slightly from the original implementation, the resultant signal is then convolved with a Morlet wavelet and the absolute value is taken in order to low-pass filter and rectify the signal. The R-Peaks are then defined as the local maxima in the processed signal. As in the original Hamilton algorithm, the custom version relies on a dynamically chosen minimal peak height and a fixed minimal distance between peaks to filter out local maxima that are not R-Peaks.

In the example, a second parameter augmentation algorithm PAA-IBI is cascaded with PAA-RP. That is, the computed parameter values CP1, CP2 of PAA-RP serve directly as inputs for PAA-IBI to compute the R-Peak Intervals for P1. The inter-beat intervals (IBI) are then computed as the time duration between subsequent R-Peaks, and thus correspond to RR-intervals. In the example, the first computed R-Peak Interval value CP-3 "704" is based on the last R-Peak which was detected prior to t1 (not shown in FIG. 6A) and the R-Peak at t1. The timestamp which is assigned to the corresponding record R3 is the timestamp t1 of the later R-Peak defining said R-Peak Interval. The signal type in the record specifies the value "704" as "IBI" (R-Peak Interval). The second computed R-Peak Interval value CP-4 "725" is based on the two R-Peaks which were detected at t2 and t1. Again, the timestamp of the later R-Peak is assigned to the corresponding record R4.

The data processor can create a single generated message mg* which includes all 4 records R1 to R4. Alternatively, it may also create multiple generated messages by grouping records into such messages. For example, a generated message may be used to include only records with computed parameter values provided by a particular PAA (e.g., mg1 with R1, R2 and mg2 with R3 and R4), or the generated message may group the records with computed parameter values timewise (e.g., mg1 with R1, R3 and mg2 with R2, R4). For the functioning of the data processor and the subsequent indexing steps it is however irrelevant how the generated messages are composed as the herein disclosed indexing approach is based on the information provided by the records within the messages.

FIG. 6B illustrates an example 620 where timestamps for records in generated messages are set using a resampling method. In the example, the incoming messages are part of an augmented message data stream already including a mix of original raw data messages m(i), m(i+1), m(i+3), m(i+k+1) and generated messages mg(i+2), mg(i+k), mg(i+k+2). The generated messages had been inserted into the incoming message stream(s) already at an earlier point in time. Each parameter augmentation algorithm (algorithm or machine learning model) has a corresponding filter function (F1 to Fn) which is adapted to filter the incoming message records for signals which are used by the respective PAA as inputs. Once the appropriate records are extracted from the messages, the PAAs process the respective filtered records to derive the computed medical health parameter values for the patients associated with the filtered records. In the previous example 610 (cf. FIG. 6A), the timestamps of the last incoming data record (serving as an input to the PAA) were set as the timestamps for the records including the resulting computed parameter values. In the example 620, more sophisticated resampling methods are applied to set the timestamps for the records in the generated messages mg*.

Box 621 illustrates the generation of common timestamps tg1 to tg6 for incoming records of different signal types exhibiting different sampling rates. Various resampling methods S1 to Sn as specified in legend table 622 can be used in this process. In general, the time information associated with a particular record of a particular generated message is computed from the time information associated with the respective records of the one or more incoming messages associated with the respective patient via resampling of the time series associated with said respective records. In general, methods for resampling said time series establish a common time grid for the timestamps of the incoming records (serving as inputs for the PAAs) and the records generated by the PAAs (outputs of the PAAs). Thereby, a PAA does not necessarily need to provide an output for each input timestamp. In each column S1 to Sn, the timestamps of the records proving the input data to the PAAs (original records) are illustrated with little circles. The timestamps of the records with the computed parameter values (resampled records) are illustrated with little black bullet points. The data processor applies 1210 the respective algorithm or machine learning model to the correspondingly filtered preprocessed (i.e., alignment of timestamps of different signal types onto common time grid) records and generates 1220 new messages for the computed parameter values (the outputs of the PAAs). As described earlier, the generated messages are inserted 1300 into the augmented data stream of messages.

Column S1 illustrates a down-sampling method for determining the timestamps of the records in the generated messages. For example, the down-sampling procedure may consist of low-pass filtering and then resampling the original signal at a new sampling rate. In the illustration every second datapoint was left out, thus down-sampling the signal by a factor 2.

Column S2 illustrates a forward fill method for determining the timestamps of the records in the generated messages. In this example, always the most recent value is kept and used in the subsequent algorithm or machine learning model until a new record of this signal type arrives.

Column S3 illustrates an interpolation method for determining the timestamps of the records in the generated messages. In this example, interpolation finds optimal new record values for timestamps on the new time grid based on the measured record values and timestamps.

Column Sn keeps the original sampling for determining the generated timestamps. This is the trivial case, if the measured record already matches the common time grid used in the further processing.

FIG. 6C illustrates an example 630 with a set 631 of cascaded PAAs 631-1 to 631-3 providing different computed medical health parameters based on original ECG raw data messages m* only. The R-Peak Detection PAA 631-1 and the Interbeat Interval Computation PAA 631-2 were already discussed in the context of FIG. 6A. The HRV Feature Estimation PAA 631-1 computes additional HRV features based on the output (IBI with timestamp) of PAA 631-2. From the IBI, 5 time-domain (SDNN, RMSSD, SDSD, pNN50, Triangular Index) and 7 frequency-domain (Total Power, VLF, LF, HF, LF norm, HF norm, LF/HF ratio) HRV measures (features) can be computed (e.g., for moving windows of 5 min). Time-domain measures are computed on each heartbeat, whereas frequency domain measures may be updated every 10 seconds. In the example, only generated records for computed SDDN values, RMSSD values and FD HF values (frequency domain high-frequency values) are illustrated. The remaining features are represented by the three dots below the record for the FD HF signal. All the computed medical health parameters are inserted into the augmented message stream 635 by the data processor via the respective generated messages mg*.

In this example, the data processor uses further PAAs 632 for monitoring the patients' Covid-19 worsening. Such Covid-PAAs 632 use records with medical state parameters of different signal types as input. For example, PAA 632-1 provides as output an artificial ventilation compliance prediction (signal type V. Comp.) for patient P1. To compute this prediction value, PAA 632-1 uses input data from the generated messages providing HRV features, from messages providing records with biomarkers, and from messages providing records with measured artificial ventilation parameters.

In an alternative embodiment, the Covid-PAAs 632 may be based on a diagnostic COVID-19 model. Tests for SARS-CoV-2 based on reverse transcriptase polymerase chain reaction (RT-PCR) are performed regularly in patients at hospital entry to avoid transmission between patients and among health care workers. The effectiveness of such a protection scheme is, however, limited by the varying sensitivity of the tests, which depends on the current viral load and thus the time passed since contracting the virus. The probability of getting a false-negative result from a RT-PCR test decreases from 100% on day 1 of infection to 67% on day 4, and it is still 38% at the time of symptom onset. On day 8 it reaches its minimum at 20% before it increases again.

Furthermore, patients infected with SARS-CoV-2 admitted to an Intensive Care Unit may not apparently suffer from COVID-19 pneumonia. Neurologic disorders in COVID-19 have been reported already in 36.4% of the patients of the Wuhan series. Rapid diagnosis of SARS-CoV-2 infection in these patients who are not primarily assigned with pneumonia is even more difficult.

A machine learning based diagnostic model has been developed to detect COVID-19. This in order to address the shortcomings of the PCR testing and to warn for repetitive testing. The dataset used for model development included laboratory and blood gas analysis findings of 255 SARS-CoV-2 positive cases and 401 negative cases including 32 influenza patients. Random Forest models were trained and tested using 5-fold nested cross-validation. The performance to detect SARS-CoV-2 positive state was measured by ROC AUC and the determined value was 0.894±0.018.

FIGS. 6A to 6C illustrate that the real-time data augmentation method comprising the steps 1100, 1200 and 1300 to enrich measured medical health parameters of patient's—in particular in an intensive care environment—with computed medical health parameters under near-real time constraints discloses a technical concept in its own which is independent of the subsequent index creation steps. The data augmentation method solves the problem to provide in near-real time a comprehensive set of medical health monitoring parameters for intensive care patients which goes beyond the set of measurable medical state parameters, thus providing a holistic view on the monitored patients' present and future health status.

Figure 7:
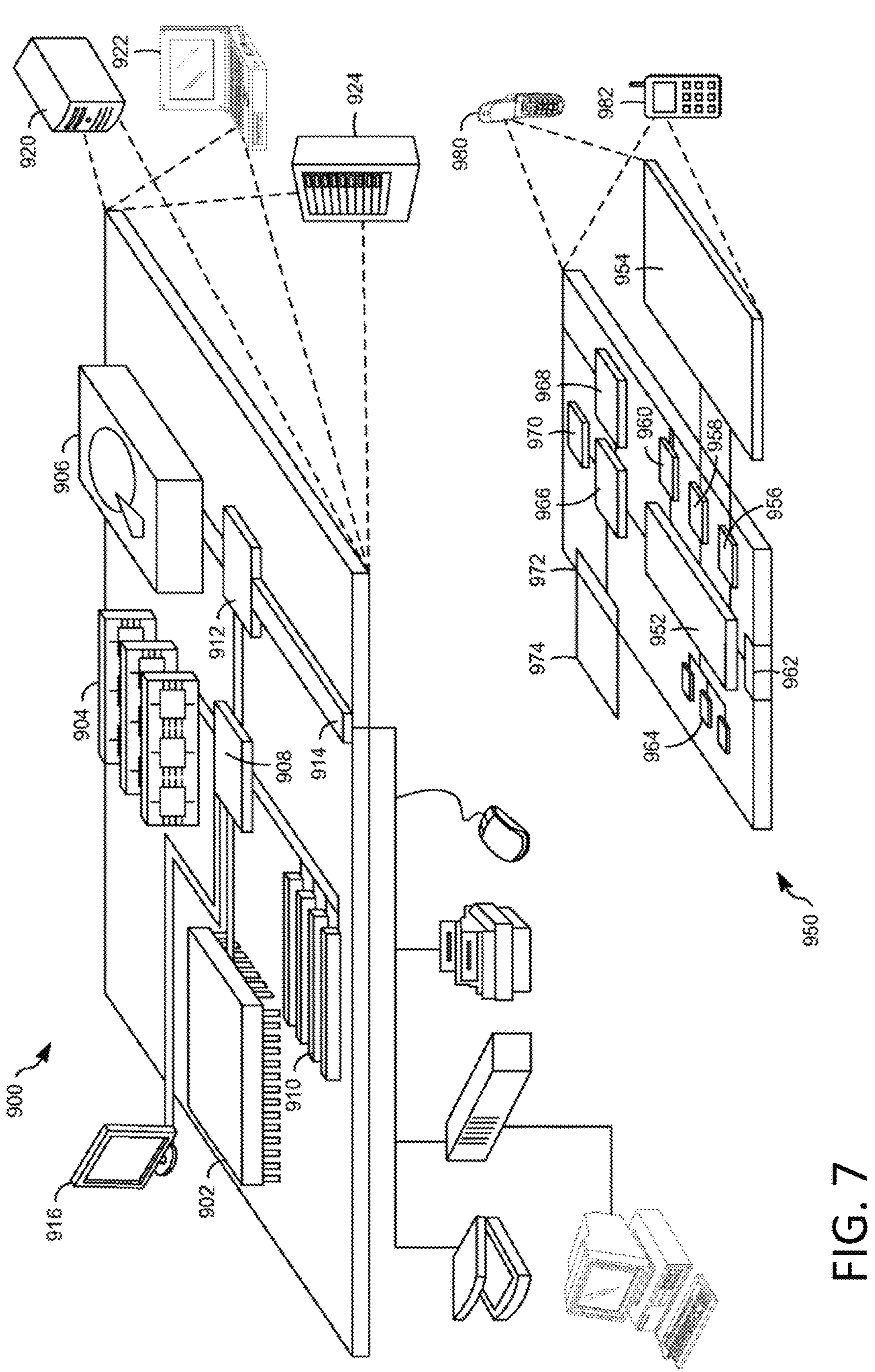
FIG. 7 is a diagram that shows an example of a generic computer device and a generic mobile computer device, which may be used with the techniques described here.

FIG. 7 is a diagram that shows an example of a generic computer device 900 and a generic mobile computer device 950, which may be used with the techniques described here. Computing device 900 is intended to represent various forms of digital computers, such as laptops, desktops, workstations, personal digital assistants, servers, blade servers, mainframes, and other appropriate computers. Generic computer device 900 may correspond to the computer system 100 of FIG. 1 for efficient index creation and enhanced real-time patient monitoring. Computing device 950 is intended to represent various forms of mobile devices, such as personal digital assistants, cellular telephones, smart phones, and other similar computing devices. For example, computing device 950 may be used as a frontend by a user (e.g., medically trained staff) to interact with the computing device 900. For example, the user may receive real-time monitoring data (e.g., an alarm) about the health state of a particular intensive care patient while treating another patient. The user can then immediately shift the focus of attention to that particular patient. The components shown here, their connections and relationships, and their functions, are meant to be exemplary only, and are not meant to limit implementations described and/or claimed in this document.

Computing device 900 includes a processor 902, memory 904, a storage device 906, a high-speed interface 908 connecting to memory 904 and high-speed expansion ports 910, and a low speed interface 912 connecting to low speed bus 914 and storage device 906. Each of the components 902, 904, 906, 908, 910, and 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as display 916 coupled to high speed interface 908. In other implementations, multiple processors and/or multiple buses may be used, as appropriate, along with multiple memories and types of memory. Also, multiple computing devices 900 may be connected, with each device providing portions of the necessary operations (e.g., as a server bank, a group of blade servers, or a multi-processor system).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 904, the storage device 906, or memory on processor 902.

The high-speed controller 908 manages bandwidth-intensive operations for the computing device 900, while the low speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a Microdrive or other device, to provide additional storage. Each of the components 950, 952, 964, 954, 966, and 968, are interconnected using various buses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processors. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provide in communication with processor 952, so as to enable near area communication of device 950 with other devices. External interface 962 may provide, for example, for wired communication in some implementations, or for wireless communication in other implementations, and multiple interfaces may also be used.

The memory 964 stores information within the computing device 950. The memory 964 can be implemented as one or more of a computer-readable medium or media, a volatile memory unit or units, or a non-volatile memory unit or units. Expansion memory 984 may also be provided and connected to device 950 through expansion interface 982, which may include, for example, a SIMM (Single In Line Memory Module) card interface. Such expansion memory 984 may provide extra storage space for device 950, or may also store applications or other information for device 950. Specifically, expansion memory 984 may include instructions to carry out or supplement the processes described above, and may include secure information also. Thus, for example, expansion memory 984 may act as a security module for device 950, and may be programmed with instructions that permit secure use of device 950. In addition, secure applications may be provided via the SIMM cards, along with additional information, such as placing the identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 984, or memory on processor 952 that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a Bluetooth, WiFi, or other such transceiver (not shown). In addition, GPS (Global Positioning System) receiver module 980 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smart phone 982, personal digital assistant, or another similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing device that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing device can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the description.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

The invention claimed is:

1. A computer-implemented method for index creation in a streaming database with medical state parameters of different types associated with a plurality of patients to allow near-real-time access to medical state parameter values reflecting medical states of patients, comprising:

receiving messages in one or more incoming data streams with each message comprising one or more records, each record having at least: a current measured medical state parameter value of a particular patient with the current measured medical state parameter value being associated with time information reflecting a time of a respective measurement, a signal identifier indicative of a type of the current measured medical state parameter value, and a patient identifier associated with the particular patient;

while receiving the one or more incoming data streams, processing incoming messages with a plurality of parameter augmentation algorithms wherein each parameter augmentation algorithm is adapted to derive additional computed medical state parameter values with respective signal identifiers for the particular patient from one or more of the incoming messages, and inserting generated messages into any of the incoming data streams, with each generated message comprising one or more records, with each record having a respective computed medical state parameter value with respective signal identifier, the patient identifier indicative of the particular patient, and time information based upon one or more records of incoming messages associated with the particular patient;

if a particular record contained in the received and in the generated messages refers to a yet unknown combination of patient identifier and signal identifier, creating a respective persisted patient-signal specific stream data table in the streaming database, and creating a block range index for the time information of the persisted patient-signal specific stream data table;

writing records contained in the received and generated messages into respective persisted patient-signal specific stream data tables of the streaming database;

updating respective block range indexes accordingly upon record insertion;

accessing, from the persisted patient-signal specific stream data tables using the respective block range indexes, the measured and computed medical state parameter values for a particular patient within a selected time interval; and providing the accessed measured and computed medical state parameter values for display on a clinical user interface in near real time to enable medical decision-making by healthcare personnel.

2. The method of claim 1, wherein a virtual stream data table of the streaming database is used as a common interface to the persisted patient-signal specific stream data tables.

3. The method of claim 1, wherein each record further comprises a bed identifier indicative for a patient bed site associated with the current measured medical state parameter value of said record.

4. The method of claim 3 further comprising:

creating a monitoring session for a particular bed site over a time interval during which data is collected from the particular bed site without intermittency and/or interruption.

5. The method of claim 1, wherein the data stream of messages is organized such that data for each patient is provided in a separate sub-stream.

6. The method of claim 1, wherein the time information associated with a particular record of a particular generated message is computed from the time information associated with the respective records of the one or more incoming messages associated with the respective patient via resampling of a time series associated with said respective records.

7. The method of claim 1, wherein the time information of a record of the generated message is set to the time associated with a latest record of the one or more incoming messages associated with the respective patient.

8. The method of claim 1, wherein the block range index for the time information of a particular persisted stream data table uses time windows adjusted to a sampling rate of the respective signal type.

9. A computer system for index creation in a streaming database with medical state parameters of different types associated with a plurality of patients to allow near-real-time access to medical state parameter values reflecting medical states of patients, comprising:

a message broker adapted to receive messages in one or more incoming data streams with each message comprising one or more records, each record having at least: a current measured medical state parameter value of a particular patient with the current measured medical state parameter value being associated with time information reflecting a time of a respective measurement, a signal identifier indicative of a type of the current measured medical state parameter value, and a patient identifier associated with the particular patient;

a stream processor adapted to:

process incoming messages with a plurality of parameter augmentation algorithms wherein each parameter augmentation algorithm is adapted to derive additional computed medical state parameter values with respective signal identifiers for the particular patient, and insert generated messages into any incoming data stream, with each generated message comprising one or more records, with each record having a respective computed medical state parameter value with respective signal identifier, the patient identifier indicative of the particular patient, and time information based upon the one or more records of incoming messages associated with the particular patient;

a data handler adapted to:

if a particular record contained in the received and generated messages refers to a yet unknown combination of patient identifier and signal identifier, create a respective persisted patient-signal specific stream data table in the streaming database, and create a block range index for the time information of the persisted patient-signal specific stream data table; and write records contained in the received and generated messages into respective persisted patient-signal specific stream data tables of the streaming database; and the streaming database adapted to:

update respective block range indexes accordingly upon record insertion, wherein the data handler is further adapted to access, from the persisted patient-signal specific stream data tables using the respective block range indexes, the measured and computed medical state parameter values for a particular patient within a selected time interval; and provide the accessed measured and computed medical state parameter values for display on a clinical user interface in near real time to enable immediate medical decision-making by healthcare personnel.

10. The system of claim 9, wherein a virtual stream data table of the streaming database is used as a common interface to the persisted patient-signal specific stream data tables.

11. The system of claim 10, wherein virtual the stream data table is partitioned by patient identifier into a plurality of virtual patient specific stream data tables, and each virtual patient specific stream data table is partitioned by signal identifier into the plurality of persisted patient-signal specific stream data tables.

12. The system of claim 9, wherein each record further comprises a bed identifier indicative for a patient bed site associated with the current measured medical state parameter value of said record, and the data handler is adapted to create a monitoring session for a particular bed site over a time interval during which data is collected from the particular bed site without intermittency and/or interruption.

13. The system of claim 9, wherein the block range index for the time information of a particular persisted stream data table uses time windows adjusted to a sampling rate of the respective signal type.

14. The system of claim 9, wherein the time information associated with a particular record of a particular generated message is either computed from the time information associated with the respective records of the one or more incoming messages associated with the respective patient via interpolation of a time series associated with the respective records, or wherein the time information of a record of the generated message is set to a time associated with a latest record of the one or more incoming messages associated with the respective patient.

15. A computer program product for index creation in a streaming database with medical state parameters of different types associated with a plurality of patients to allow near-real-time access to medical state parameter values reflecting medical states of patients, the computer program product being tangibly embodied on a non-transitory computer-readable storage medium and comprising instructions that, when executed by at least one computing device, are configured to cause the at least one computing device to:

receive messages in one or more incoming data streams with each message comprising one or more records, each record having at least: a current measured medical state parameter value of a particular patient with the current measured medical state parameter value being associated with time information reflecting a time of a respective measurement, a signal identifier indicative of a type of the current measured medical state parameter value, and a patient identifier associated with the particular patient;

while receiving the one or more incoming data streams, process incoming messages with a plurality of parameter augmentation algorithms wherein each parameter augmentation algorithm is adapted to derive additional computed medical state parameter values with respective signal identifiers for the particular patient from one or more of the incoming messages, and insert generated messages into any of the incoming data streams, with each generated message comprising one or more records, with each record having a respective computed medical state parameter value with respective signal identifier, the patient identifier indicative of the particular patient, and time information based upon one or more records of incoming messages associated with the particular patient;

if a particular record contained in the received and in the generated messages refers to a yet unknown combination of patient identifier and signal identifier, create a respective persisted patient-signal specific stream data table in the streaming database, and creating a block range index for the time information of the persisted patient-signal specific stream data table;

write records contained in the received and generated messages into respective persisted patient-signal specific stream data tables of the streaming database;

updating respective block range indexes accordingly upon record insertion;

access, from the persisted patient-signal specific stream data tables using the respective block range indexes, the measured and computed medical state parameter values for a particular patient within a selected time interval; and provide the accessed measured and computed medical state parameter values for display on a clinical user interface in near real time to enable immediate medical decision-making by healthcare personnel.

16. The computer program product of claim 15, wherein a virtual stream data table of the streaming database is used as a common interface to the persisted patient-signal specific stream data tables.

17. The computer program product of claim 15, wherein each record further comprises a bed identifier indicative for a patient bed site associated with the current measured medical state parameter value of said record.

18. The computer program product of claim 17, wherein the instructions, when executed by the at least one computing device, are further configured to cause the at least one computing device to:

create a monitoring session for a particular bed site over a time interval during which data is collected from the particular bed site without intermittency and/or interruption.

19. The computer program product of claim 15, wherein the data stream of messages is organized such that the data for each patient is provided in a separate sub-stream.

20. The computer program product of claim 15, wherein the time information associated with a particular record of a particular generated message is computed from the time information associated with the respective records of the one or more incoming messages associated with the respective patient via resampling of a time series associated with said respective records.

* * * * *